(12) United States Patent
Lakin

(10) Patent No.: US 7,175,664 B1
(45) Date of Patent: Feb. 13, 2007

(54) PROSTHETIC HAVING A MODULAR SOFT TISSUE FIXATION MECHANISM

(75) Inventor: Christina Lakin, Warsaw, IN (US)

(73) Assignee: Biomet, Inc., Warsaw, IN (US)

( * ) Notice: Subject to any disclaimer, the term of this patent is extended or adjusted under 35 U.S.C. 154(b) by 243 days.

(21) Appl. No.: 10/189,639

(22) Filed: Jul. 3, 2002

(51) Int. Cl.
 *A61F 2/40* (2006.01)
(52) U.S. Cl. .................................. 623/19.14
(58) Field of Classification Search ............ 623/18.11, 623/19.11–19.14
 See application file for complete search history.

(56) References Cited

U.S. PATENT DOCUMENTS

| | | | |
|---|---|---|---|
| 2,719,522 A | 10/1955 | Hudack | |
| 3,803,641 A | 4/1974 | Golyakhovsky | |
| 3,859,669 A | 1/1975 | Shersher | |
| 3,979,778 A | 9/1976 | Stroot | |
| 4,045,825 A | 9/1977 | Stroot | |
| 4,045,826 A * | 9/1977 | Stroot | 623/19.11 |
| 4,714,475 A | 12/1987 | Grundei et al. | |
| 5,194,066 A | 3/1993 | VanZile | |
| 5,282,867 A | 2/1994 | Mikhail | |
| 5,314,479 A * | 5/1994 | Rockwood et al. | 623/19.14 |
| 5,330,531 A | 7/1994 | Capanna | |
| 5,358,526 A * | 10/1994 | Tornier | 623/19.14 |
| 5,702,486 A * | 12/1997 | Craig et al. | 623/19.14 |
| 6,126,695 A * | 10/2000 | Semlitsch | 623/22.15 |
| 6,127,596 A | 10/2000 | Brown et al. | |
| 6,165,223 A | 12/2000 | Metzger et al. | |
| 6,264,699 B1 | 7/2001 | Noiles et al. | |
| 6,283,999 B1 | 9/2001 | Rockwood | |
| 6,398,812 B1 * | 6/2002 | Masini | 623/19.14 |
| 6,520,994 B2 * | 2/2003 | Nogarin | 623/19.14 |
| 6,558,425 B2 * | 5/2003 | Rockwood, Jr. | 623/19.12 |
| 6,592,622 B1 | 7/2003 | Ferguson | |

FOREIGN PATENT DOCUMENTS

FR    2634373    7/1998

\* cited by examiner

Primary Examiner—Eduardo C. Robert
(74) Attorney, Agent, or Firm—Harness, Dickey & Pierce, P.L.C.

(57) ABSTRACT

A multi-piece prosthetic component for use in joint arthroplasty which is adapted to be implanted into a joint and engaged by a joint socket. The modular prosthetic component includes body which is at least partially implantable within a bone, said body having an external surface. A mechanism for coupling soft tissue to the exterior surface of the implant is provided. The mechanism has an attachment mechanism which is operable to prevent movement of the soft tissue attachment mechanism with respect to the body.

29 Claims, 7 Drawing Sheets

PROSTHETIC HAVING A MODULAR SOFT TISSUE FIXATION MECHANISM

BACKGROUND OF THE INVENTION

1. Field of the Invention

This invention relates generally to a method and apparatus for use in orthopedic surgery and, more particularly, to a method and apparatus for providing a prosthesis having a modular soft tissue coupling mechanism. The soft tissue coupling mechanism is a member configured to be optionally coupled to the implant and has a fixation flange capable of being coupled to soft tissues.

2. Discussion of the Related Art

It is generally known in the art to provide prostheses that replace or reinforce various portions of bone during an orthopedic surgical procedure. However, the current prior art prostheses along with the associated surgical components and instruments utilized during orthopedic surgery suffer from many disadvantages.

For example, because the extent of degradation is not always evident until during the surgery; extensive bone resection may be necessary. Additionally, etiologies such as bone tumors or those requiring revision of an implanted joint require significant bone removal which may remove soft tissue fixation sites. In these cases, soft tissue fixation to the prosthesis may or may not be necessary. To provide for soft tissue attachment, some replacement joint components provide an integral flange configured to accept soft tissue attached to a lateral surface of the prosthetic replacement joint head. These fixed fixation flanges, however, may not provide the proper locational adaptivity needed during the orthopedic surgical procedure and leave the surgeon with little or no options as to soft tissue attachment.

What is needed then is a prosthesis and associated surgical components for use in orthopedic surgery which does not suffer from the above-mentioned disadvantages. This in turn, will provide a prosthesis which is stable and secure and increases the overall flexibility for a surgeon to fix soft tissues. It is, therefore, an object of the present invention to provide such a prosthesis and associated surgical components for use in orthopedic surgery.

SUMMARY OF THE INVENTION

In accordance with the teachings of the present invention, an apparatus and method for providing a prosthetic having a modular soft tissue attachment mechanism is disclosed. The apparatus and method employs a modular soft tissue attachment mechanism for use during the orthopedic surgical procedure.

In one embodiment, an orthopedic implant has a body that is at least partially implantable within a bone. A mechanism for coupling soft tissue to the body is provided. The mechanism for coupling soft tissue to the body has an attachment mechanism operable to prevent movement of the coupling mechanism with respect to the body.

In another embodiment, a humeral prosthetic having an articulating head is presented. The humeral prosthetic has a base member defining a fixation surface which is coupled to the head. A soft tissue fixation member has a coupling mechanism, which functions to couple the soft tissue fixation member to the fixation surface. A locking mechanism is provided which prevents movement of the soft tissue fixation mechanism with respect to the base member.

In another embodiment, a modular replacement joint component is used for joint arthroplasty such that a replacement joint component is adapted to be implanted into a bone and engaged by a socket portion of the replacement joint component. The replacement joint component includes a head member having a first articulating surface and a second medial surface, which is opposite to the first articulating surface. The first articulating surface is adapted to engage the articulating surface of the a socket portion and the second medial surface is adapted to engage a second fixation component. The fixation component has a first surface adapted to be secured to the lateral surface of the head member and a second surface. The base member extends from the second medial surface such that the base member provides a fixation surface. A soft tissue fixation member, is coupled to the base member. The soft tissue fixation member has an exterior flange having a soft tissue coupling member.

A method for implanting an orthopedic devise is further disclosed. The method includes selecting an appropriately sized implant. Next, a determination is made if soft tissue fixation to the implant is necessary. Should it be necessary to couple soft tissue to the implant, a soft tissue fixation mechanism is attached to the implant. The implant is subsequently implanted.

Use of the present invention provides an apparatus and method for providing a prosthetic having a modular soft tissue attachment mechanism for use during an orthopedic surgical procedure. As a result, the aforementioned disadvantages associated with the currently available prostheses and associated surgical components have been substantially reduced or eliminated.

BRIEF DESCRIPTION OF THE DRAWINGS

Still other advantages of the present invention will become apparent to those skilled in the art after reading the following specification and by reference to the drawings in which.

DETAILED DESCRIPTION OF THE PREFERRED EMBODIMENTS

The following description of the preferred embodiments concerning an apparatus and method for providing a prosthesis having a modular soft tissue attachment mechanism is merely exemplary in nature and is in no way intended to limit the invention, its application, or uses. Moreover, while the present invention is discussed in detail in relation to a shoulder joint and a hip joint replacement, the present invention is not limited to only these procedures. For example, any type of orthopedic surgical procedure that replaces or reinforces bone may employ the present invention.

Figure 1:
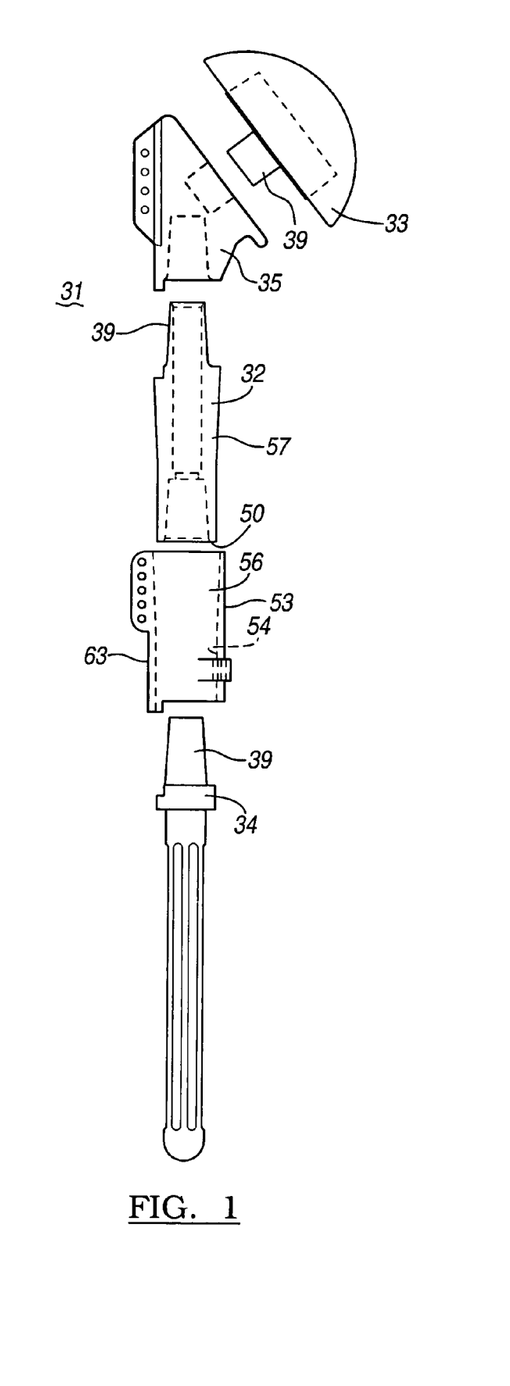
FIG. 1 is an exploded view of the prosthetic component according to the teachings of the preferred embodiment.
Figures 9, 10:
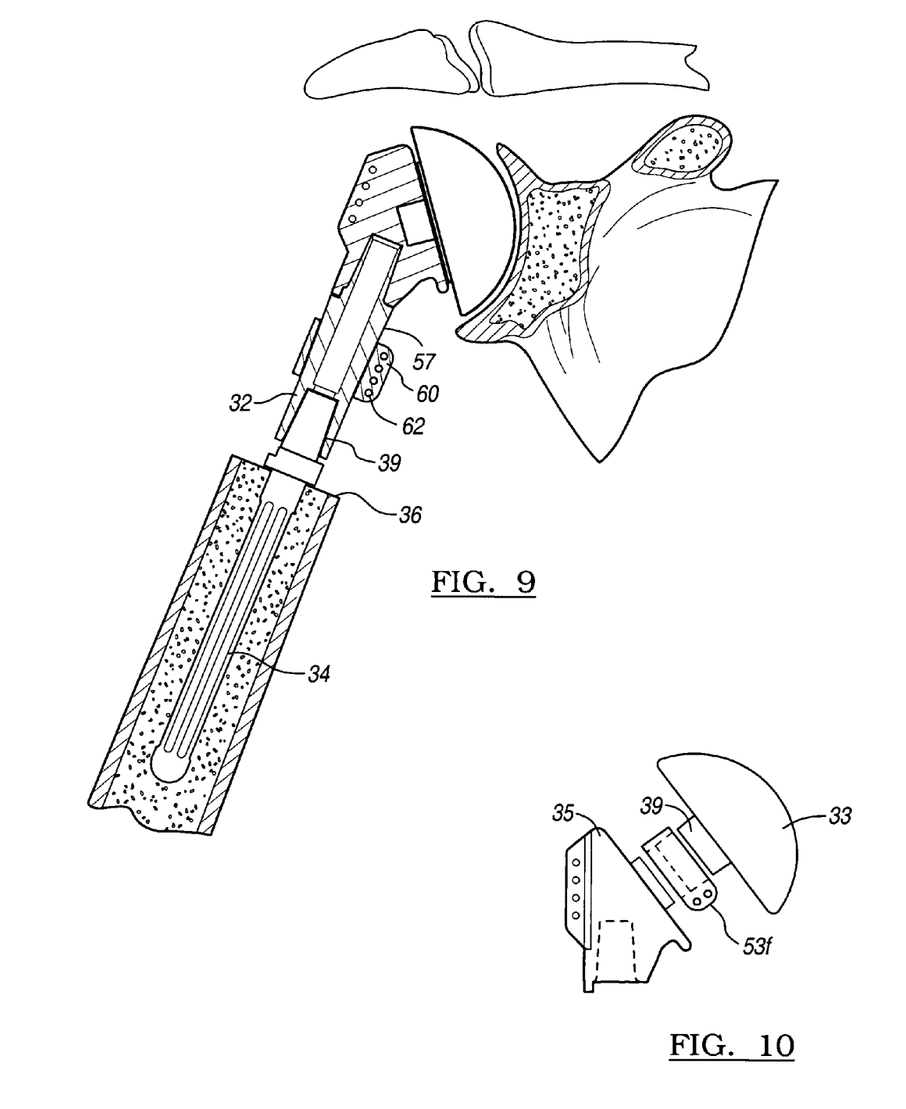
FIG. 9 represents the prosthetic according to the present invention implanted within a skeletal structure.
FIG. 10 represents an alternate embodiment of the present invention.

FIG. 1 depicts components used in a shoulder arthroplasty of the current invention. As shown, a modular humeral component 31 has a base member 32 and a head member 33. The base member 32 is configured to be coupled to a fixation stem 34 which is used to attach the humeral component 31 to a resected bone 36 of the humerus 38 by way of a Morse type taper 39 or any other attachment mechanism (see FIG. 9). If a total shoulder arthroplasty is performed, a glenoid component 40, shown in FIG. 9, is first implanted into the scapula 42 using techniques well known in the art. The glenoid component 40 is preferably of the type disclosed in U.S. Pat. No. 5,800,551, which is hereby incorporated by reference, or any other suitable conventional glenoid component. The humeral component 31 is designed to allow rotational and transitional movement of the head member 33 with respect to the glenoid component 40.

FIG. 1, shows a humeral head 33 which mates through a humeral body component 35 to the base member 32 by way of a Morse type taper 39 or any other appropriate attachment mechanism. It should be noted that a surgical kit of the components would contain numerous head members 33, each having a varied radius of curvature, diameter, and height to allow a surgeon to optimize joint movement. Additionally, a surgical kit would contain the instruments needed for implantation (described later).

Figure 2A:
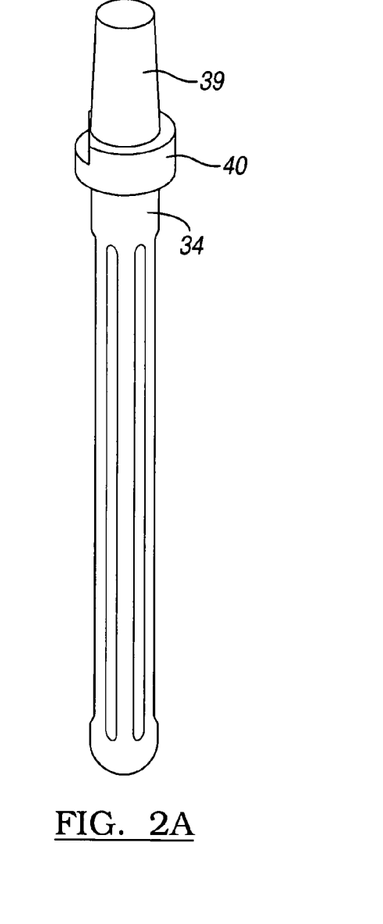
FIGS. 2a–2b are views of a bone fixation member of humeral component of FIG. 1.
Figure 2B:
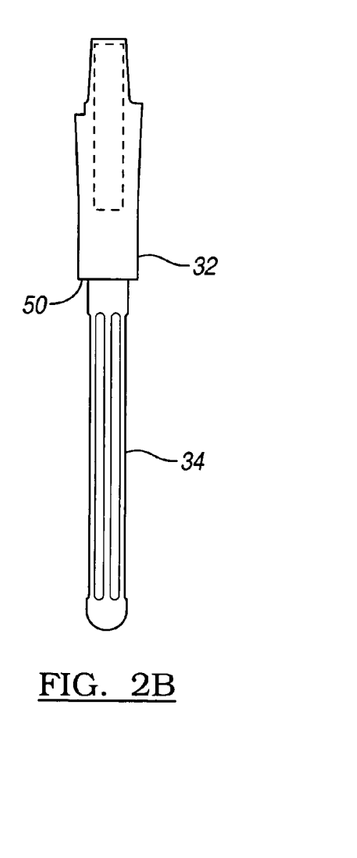

FIGS. 2a and 2b depict fixation stems 34 according to the teachings of the present invention. FIG. 2a discloses a conventional fixation stem which will be mounted to the base member 32 via a Morse type taper 39. The Morse type taper 39 is disposed upon a shelf member 40 which functions as an interface surface to a resected bone (as described below). Alternatively, as depicted in FIG. 2b, the fixation stem 34 can be integral to the base member 32. Particularly, the stem 34 is disposed perpendicularly to the surface 50 of the base member 32. In this configuration, however, the surface 50 must be configured so as to allow the interior bore 56 of the soft tissue fixation mechanism 53 to be disposed about the base member 32.

Figure 3:
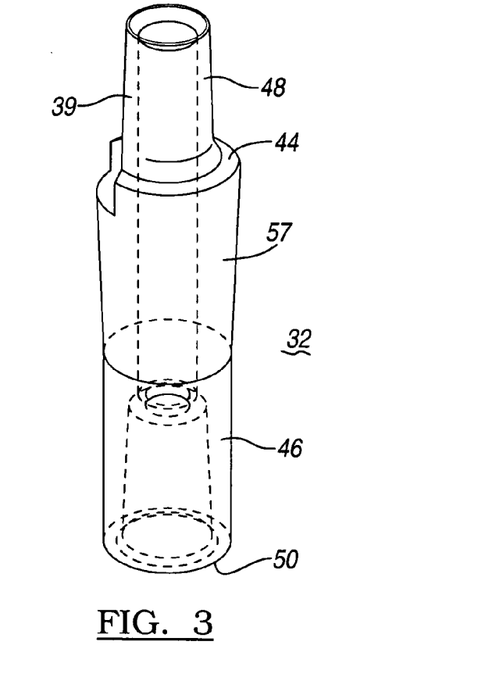
FIG. 3 represents a base member according to the teachings of the present invention.

FIG. 3 depicts the base member 32 of one embodiment of the current invention. The base member 32 is defined by a shelf member 44, which may function as an impaction surface. The shelf member 44 can have at least one mating member 48 for engaging the humeral body component 31. It is preferred that the mating member 48 be a defined Morse type taper 39 or other suitable attaching mechanism. In addition to the mating member 48, each base member 32 has or is coupled to a fixation stem 34 disposed on the lower lateral surface 50. The fixation stem 34 is generally perpendicular to the lower lateral surface 50, and can be a male or female Morse type taper. A cylindrical outer surface 46 of the base member 32 is defined between the shelf member 44 and the flat lower lateral surface 50. Optionally, disposed about the base member 32 is soft tissue fixation mechanism 53. Soft tissue fixation mechanism 53 is a cylindrical tube having an inner surface 54, which defines the inner bore 56 and an exterior surface 63.

The humeral body component 31, stem 34, base member 32, and soft tissue fixation mechanism 53 is made of bio-compatible materials such as, without limitation, titanium, titanium alloys, surgical alloys, stainless steels, biocompatible ceramics, and cobalt alloys. Optionally, the base member 32 can additionally be made of materials such as biocompatible ceramics and resorbable and non-resorbable polymers and other anticipated bio-compatible metallic or polymeric materials. Should the base member 32 be made of non-metallic components, a fastener may be needed to couple the body 31 to the base member 32. Additionally, the fixation mechanism 53 can be an allograft material.

Figure 4:
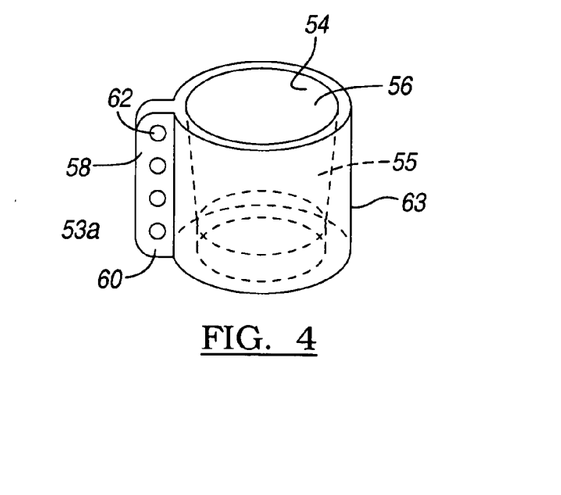
FIGS. 4–8 are alternate embodiments for a soft tissue fixation member of the humeral component of the present invention.
Figure 5:
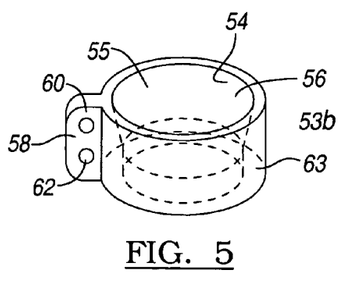
Figure 6:
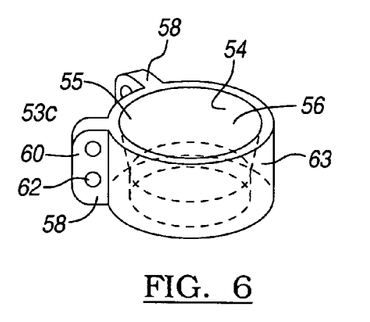

As best seen in FIGS. 4–8, the soft tissue fixation mechanisms 53a–e are configured to be annularly disposed about the cylindrical outer surface 46 of the base member 32. The inner surface 54 is configured to have an attachment mechanism 55 disposed thereon. Optionally, this attachment mechanism 55 can take the form of a 6° included Morse type taper which couples to a Morse type taper 57 defined on the cylindrical outer surface 46 of the base member. The exterior surface 63 of the soft tissue fixation mechanism 53a–f define soft tissue fixation members 58. As best seen in FIG. 4, the soft tissue fixation members 58 can take the form of a longitudinal flange 60. The longitudinal flange 60 defines through suture bores 62 which function as sites for coupling soft tissue to the prosthetic. Alternately, the soft tissue fixation members 58 can take the form of multi-directional flanges 64 or as an attachable suture anchor attachment site. The use of a Morse type taper 55 to couple the soft tissue fixation member 58 to the base member 32 allows a physician to rotate at any desired location the location of the fixation flanges.

FIGS. 4–8 depict alternate embodiments of soft tissue fixation mechanism 53a–53e. In this embodiment, the soft tissue fixation mechanisms 53a–53e are cylindrical members which define an interior bore 56. The interior bore 56 defines an attachment mechanism 58. Additionally, depending on the length of the soft tissue fixation mechanism 53a–e, a through suture bore 62 can be defined. The attachment mechanism 55 is a female portion of a 6° Morse type taper. The 6° included Morse type taper couples to the 6° included Morse type taper defined on the exterior surface of base 32. As can be seen in FIGS. 4, 5, 6, and 8, the soft tissue fixation mechanism 53 has an exterior surface 63 which defines at least one soft tissue coupling flange 60. This flange 60 is generally coaxial with the body of the implant and is generally parallel to the implant centerline.

Figure 7:
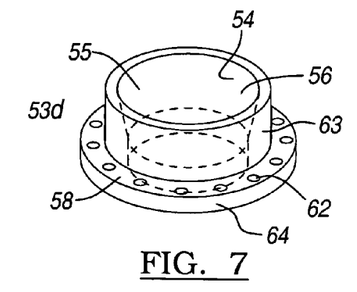
Figure 8:
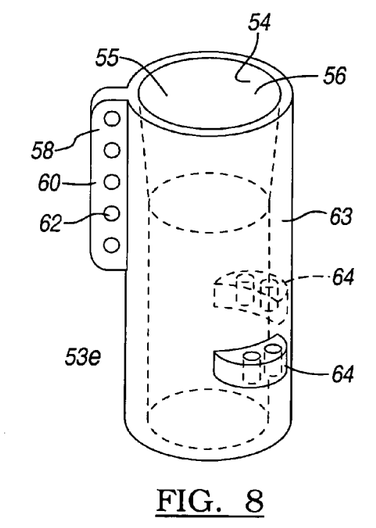

As can be seen in FIGS. 7 and 4, the flange 64 can also be configured so as to define a plane perpendicular to the centerline of the base member 32. Each flange 64 defines at least one through suture bore 62 or slot which is used to couple the soft tissue to the soft tissue fixation mechanism 53a–e. It should be noted that each soft tissue fixation mechanism 53a–53e can have a plurality of flanges 64 and 60. While through suture bores 62 are shown for use to couple the soft tissue, those skilled in the art will recognize other structures such as keyed slots and channels and angled flange members can be used to accept sutures and suture anchors. Additionally, wires, aortic graft, and tape can be used to fix the soft tissue.

FIG. 9 discloses the orthopedic implant 31 shown in FIG. 1 disposed within a patient. Shown is the bone fixation stem 34 disposed within the medullary canal of the resected bone 36. The stem 34 is coupled to the base member 32 via a Morse type taper 39. Disposed about the base member 32 is the soft tissue fixation mechanism 53a. As can be seen, the mounting flange 60 can be rotated about the base member 32 to fix extensor and abductor soft tissue to the prosthetic 31. In situations where the flexor abductor must be fixed to the prosthetic, a soft tissue attachment mechanism such as the one shown in FIG. 4 can be used.

FIG. 10 discloses an alternate view of the present invention. Shown is a soft tissue fixation mechanism 53f disposed between a humeral head 33 and a humeral head base 35. As with the soft tissue fixation members depicted in FIGS. 4–8, it is envisioned that the soft tissue fixation mechanism 53f can have either longitudinal or transverse mounting flanges.

As shown in FIGS. 11–15, the attachment mechanism 55 need not be a Morse type taper. FIGS. 13a and 13b show the attachment mechanism 55 being tapered key slots 66 which couple to a locking flange 68 disposed on the base member 32. It is envisioned that as few as one and as many as sixteen tapered key slots 66 can be disposed on the inner surface 54 of the soft tissue fixation member 53. Base members, as disclosed in FIG. 11, would be used in situations where maximum rotational torque may be applied by the soft tissue to the prosthetic. In this regard, while a Morse type taper fixation is usable in a humeral prosthetic, a key/slot configuration may be necessary for a higher rotational stability.

Figure 11:
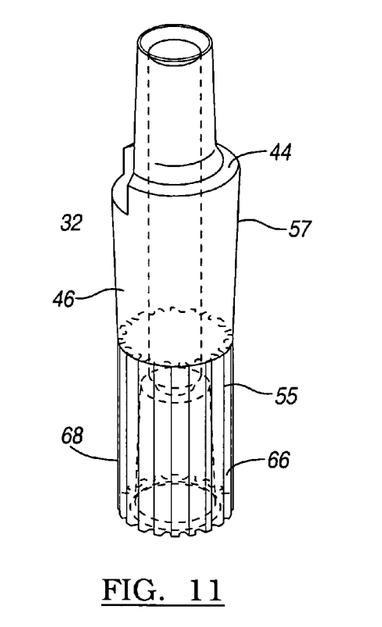
FIG. 11 represents an alternate base member according to the teaching of the present invention.
Figure 12:
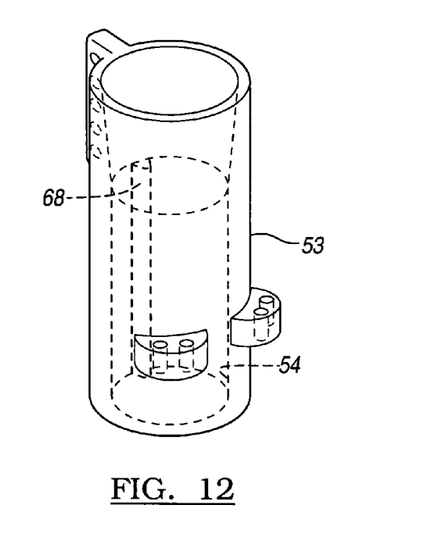
FIG. 12 represents an alternate soft tissue fixation member according to the teaching of the present invention.
Figure 13A:
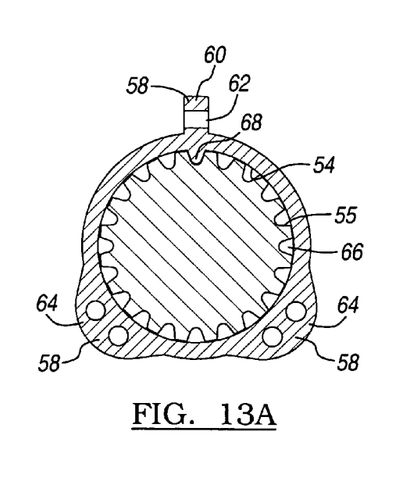
FIGS. 13a–13b represent the interaction of the soft tissue fixation member of FIG. 12 with the base according to FIG. 11.
Figure 13B:
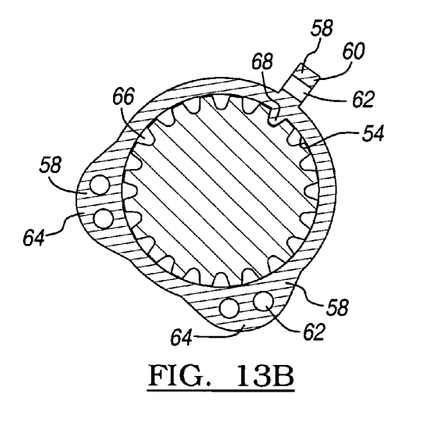

FIG. 11 defines base members 32 having the shelf member 44 and a cylindrical outer surface 46. Additionally shown is a channeled outer surface 68 for mating the base member 32 to the soft tissue fixation members 58. The base members 32 and soft tissue fixation members 58 are depicted in FIGS. 13a and 13b and are shown mated. As can be seen, locking flange 68 is disposed on the inner surface 54 of the soft tissue fixation member 58. This locking flange 68 is coupled to a channel formed on the exterior surface of the base 32. FIG. 13b shows the rotation of the soft tissue fixation members 58 about the base member 32, which allows the physician to regulate or adjust the location of the optional fixation flange.

The method for implanting the humeral component 30, along with associate surgical components utilized will now be described with reference to FIG. 16. The head of the humerus 38 is resected using a saw, then planed flat. With the resected bone 36 of the humerus 38 exposed, an appropriately sized implant is chosen for insertion into the medullary canal of the humerus.

Once the proper sized implant is chosen, the resected bone 36 of humerus 38 is optionally reamed using a reamer shaft with the driver. Upon rotating the surface of the reamer, the resected bone 36 of the humerus 38 is prepared to mate or conform with the shape of the fixation stem 34 of the base member 32.

Once the inside surface of the resected bone 36 of the humerus 38 has been prepared, the stem 34 can be inserted into the medullary canal. Prior to insertion, a decision is made whether soft tissue fixation to the implant is necessary. Should it be necessary, a soft tissue fixation mechanism 53 is disposed about the base member 32. The soft tissue fixation mechanism 53 is rotated into position and fixed to the base member 32 in its proper orientation. It is envisioned that fixation stem 34 of the base member 32 can be forced into the medullary canal to displace the bone material. Optionally, the medullary canal can also be reamed to a larger interior diameter to accept the stem 34 without displacement of the bone material.

The modular nature of the humeral component 30 of the present invention allow a set of various types of both replacement base members 32, humeral body components 31, and stems 34 to be formed. In using such a set, a surgeon can interoperatively choose the appropriate base member depending on the patient's particular condition. Additionally, the surgeon can then choose from a set of head members 33, which both have the proper articulating surface radius and a proper coupling to the humeral body component 31.

Figures 14, 15:
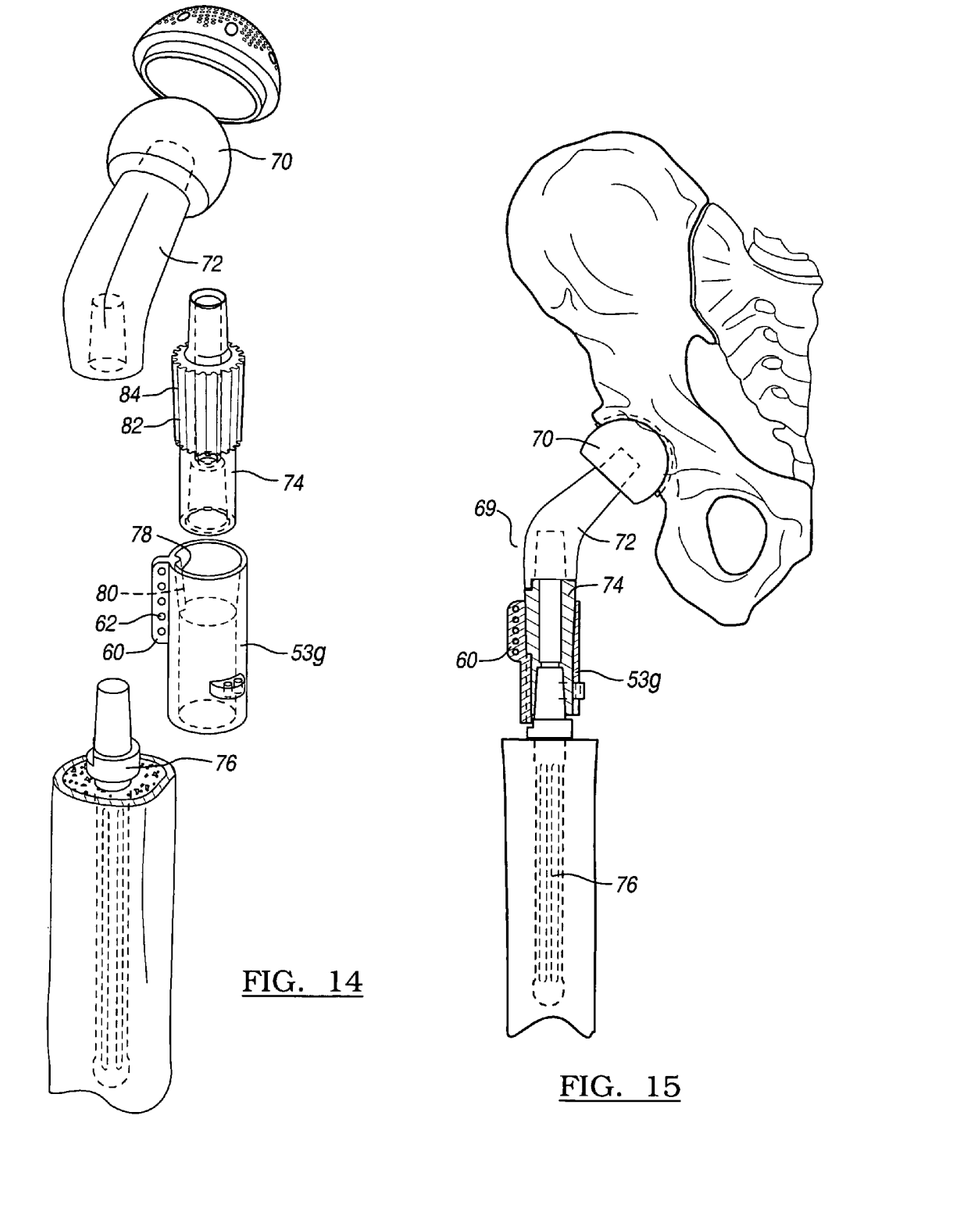
FIGS. 14 and 15 represent the application of the present invention to a femoral implant.

FIGS. 14 and 15 show the soft tissue fixation member according to the present invention used in a hip implant. FIG. 14 depicts an exploded view of an implant having a head portion 70 with a neck 72. Additionally, the prosthetic has base portion 74 and a femoral stem 76. Under normal conditions, the femoral prosthetic 69 can be assembled without the use of a soft tissue fixation mechanism 53g. Soft tissue fixation mechanism 53g is shown having an interior locking mechanism 78 taking the form of a tapered flange 80. The tapered flange 80 is configured so as to be lockably positioned within a channel 82 disposed on an exterior surface 84 of the base portion 74. As can be seen, the soft tissue fixation mechanism 53g is rotatable about the base portion 74, allowing the soft tissue coupling flange 86 to be rotationally positioned in any location about the centerline of the implant.

FIG. 15 depicts the soft tissue fixation mechanism 53g according to the teachings of the present invention disposed about the hip prosthetic. In this configuration, the head 70 is disposed within the acetabulum. The neck 72 is coupled to the base portion 74 and the base portion 74 is coupled to the stem 76 using a standard locking Morse type taper 88.

Figure 16:
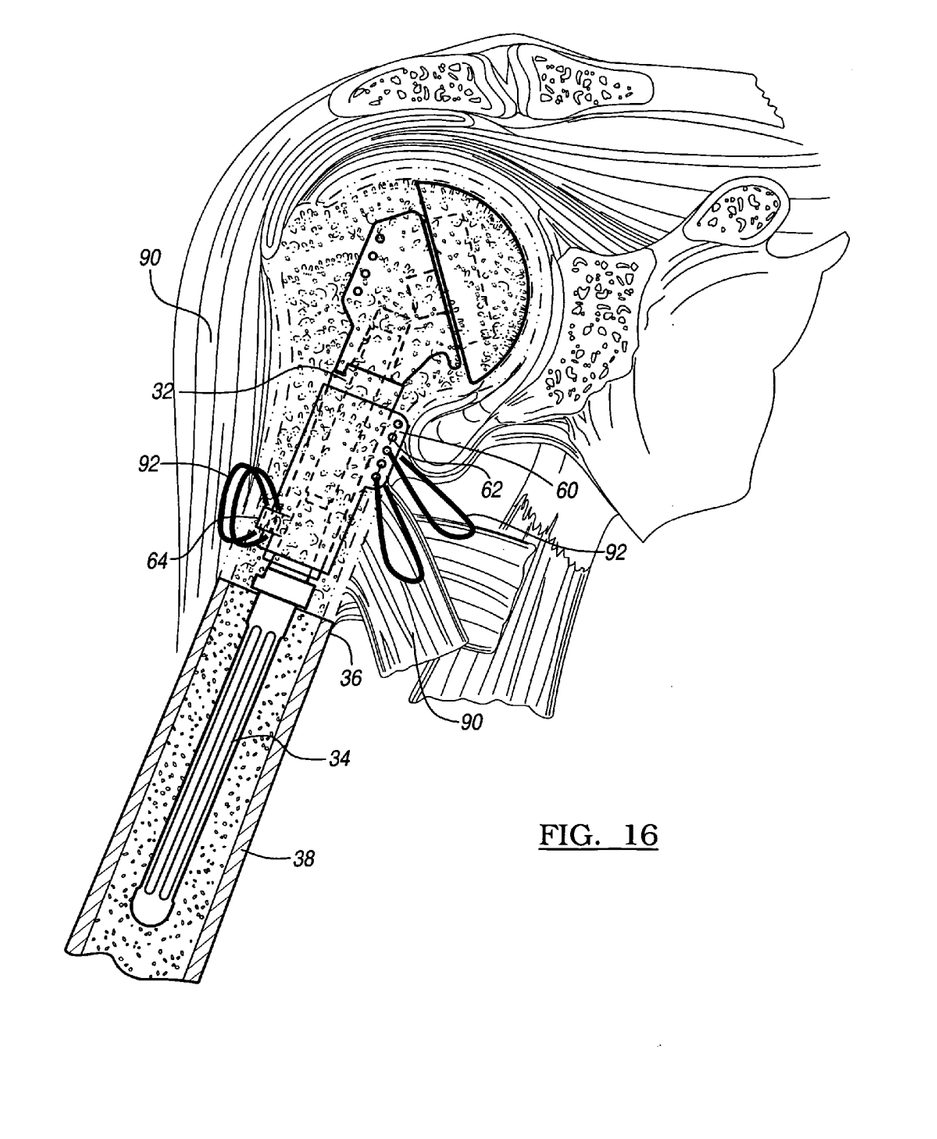
FIG. 16 represents cross-sectional views of implanted humeral components of the present invention and its fixation to soft tissue.

FIG. 16 depicts the coupling of soft tissue to varying flanges 60 and 64 of the prosthetic. Generally, the implant will be implanted into the medullary canal of the resected bone 36 prior to the coupling of the soft tissue 90 to the soft tissue fixation mechanism 53a. As can be seen, the soft tissue 90 is coupled to the soft tissue attachment mechanism via standard sutures 92 or suture anchors, while the attachment mechanism can take the form of a threaded fastener or appropriate adhesive.

While the soft tissue attachment mechanism is shown throughout the application as a cylindrical tube disposed about a implant positioned within an intermedullary canal, it should be noted that the soft tissue fixation member 53 can further take the form of a plate coupled to either a cylindrical or flat baseplate member. In this regard, the soft tissue fixation mechanism 53 can take the form of a plate member capable of accepting a suture or suture anchor. Additionally, the prosthetic need not be associated with a joint, e.g. an intercalary member.

Additionally, the soft tissue fixation mechanism 53 can be adjustably positioned on the prosthetic in one or more fixation areas. In this regard, multiple soft tissue fixation mechanisms can be located on multiple locations of a single implant. While the soft tissue fixation mechanism 53 is shown on a modular prosthetic, those skilled in the art will recognize that only the soft tissue fixation mechanism 53 need be modular and that the soft tissue fixation mechanism 53 can be fixed to a single piece prosthetic device.

The description of the invention is merely exemplary embodiments in the present invention. One skilled in the art would readily recognize from such discussion and from accompanying drawings and claims that various changes, modifications, variations may be made therein without the spirit and scope of the invention. For example, while the soft tissue fixation mechanism 53 is shown being coupled to a humeral or femoral implant, the soft tissue fixation mechanism 53 can equally be applied to other joint implants such as, but not limited to, knees and elbows, and for whole bone replacement. Additionally, while the base member is shown being disposed outside of an intermedullary canal, it is possible to position at least a portion of the base member 32 within a bone structure. Further, while the fixation members are shown as transverse and longitudinal flanges, they can equally be positioned in any direction, or can take the form of a depression within the surface of the soft tissue fixation mechanism exterior.

What is claimed is:

1. An orthopedic implant configured to be attached to a bone comprising:
   an implant having an articulating surface and a bone attachment region forming a complete functional implant configured to be implanted into a bone; and
   a soft tissue fixation member operable to be attached to said implant with a locking mechanism, wherein said locking mechanism is configured to prevent movement of the fixation member with respect to the implant and wherein said complete implant is configured to be implanted into the bone in a first functional configuration with the soft tissue fixation member and in a second functional configuration without the soft tissue fixation member.

2. The orthopedic implant according to claim 1 wherein the bone attachment region defines a taper and wherein the locking mechanism is a Morse type taper.

3. The orthopedic device according to claim 1 wherein the soft tissue fixation member is a second flange defining a suture bore therethrough.

4. The orthopedic device according to claim 3 wherein the second flange defines a plurality of suture bores.

5. The orthopedic device according to claim 3 wherein said bone attachment region is an exterior cylindrical surface which defines an axis, said second flange being parallel to said axis.

6. The orthopedic device according to claim 5 further having a second soft tissue fixation member.

7. An orthopedic implant configured to be attached to a bone comprising:
   an implant having an articulating surface and a bone attachment region forming a complete implant configured to be implanted into a bone; and
   a soft tissue fixation member operable to be attached to said implant with a locking mechanism, wherein said locking mechanism is configured to prevent movement of the fixation member with respect to the implant and wherein said complete implant is configured to be implanted into the bone in a first configuration with the soft tissue fixation member or in a second configuration without the soft tissue fixation member, wherein said bone attachment region defines a channel and wherein said locking mechanism is a flange.

8. An orthopedic implant configured to be attached to a bone comprising:
   a body defining an attachment region and a bone engagement region; and
   a soft tissue fixation member operable to be attached to said attachment region with a locking mechanism, wherein said locking mechanism is configured to prevent movement of the fixation member with respect to the body, wherein said attachment region defines a channel and wherein said locking device mechanism is a flange coupled to the channel, wherein said body is configured to be implanted into a bone in a first configuration with the soft tissue fixation member or in a second configuration without the soft tissue fixation member.

9. An orthopedic implant configured to be attached to a bone comprising:
   an implant having an articulating surface and a bone attachment region forming a complete implant configured to be implanted into a bone; and
   a soft tissue fixation member operable to be attached to said implant with a locking mechanism, wherein said locking mechanism is configured to prevent movement of the fixation member with respect to the implant and wherein said complete implant is configured to be implanted into the bone in a first configuration with the soft tissue fixation member or in a second configuration without the soft tissue fixation member, wherein said bone attachment region defines a channel and wherein said locking mechanism is a flange, wherein the bone attachment region defines a plurality of channels.

10. An orthopedic implant configured to be attached to a bone comprising:
    an implant having an articulating surface and a bone attachment region forming a complete implant configured to be implanted into a bone; and
    a soft tissue fixation member operable to be attached to said implant with a locking mechanism, wherein said locking mechanism is configured to prevent movement of the fixation member with respect to the implant and wherein said complete implant is configured to be implanted into the bone in a first configuration with the soft tissue fixation member or in a second configuration without the soft tissue fixation member, wherein the soft tissue fixation member is a second flange defining a suture bore therethrough, wherein said bone attachment region is an exterior cylindrical surface which defines an axis, said second flange being parallel to said axis wherein the bores are radially disposed about said cylindrical surface.

11. An orthopedic implant configured to be attached to a bone comprising:
    an implant having an articulating surface and a bone attachment region forming a complete implant configured to be implanted into a bone; and
    a soft tissue fixation member operable to be attached to said implant with a locking mechanism, wherein said locking mechanism is configured to prevent movement of the fixation member with respect to the implant and wherein said complete implant is configured to be implanted into the bone in a first configuration with the soft tissue fixation member or in a second configuration without the soft tissue fixation member, wherein the soft tissue fixation member is a second flange defining a suture bore therethrough, wherein the second flange defines a plurality of suture bores, wherein said bores define a line parallel to said axis.

12. A humeral prosthetic comprising:
    a head portion having an articulating surface;
    a base member having a bone engaging surface defining a taper, said bone engaging surface coupled directly to said head portion to form a complete implantable prosthetic, said base member defining an outer fixation surface, said base member having a locking mechanism; and
    an attachable soft tissue fixation member having a coupling mechanism, wherein said coupling mechanism functions to couple the soft tissue fixation member to the outer fixation surface, wherein said locking mechanism is configured to prevent movement of the soft tissue fixation member with respect to the base member.

13. The humeral component according to claim 12 wherein said locking mechanism is a Morse type taper.

14. The humeral prosthetic according to claim 12 wherein said fixation member is a flange.

15. The humeral prosthetic according to claim 14 wherein said flange is parallel to a defining axis of said base member.

16. The humeral prosthetic according to claim 14 wherein said fixation member defines a flange perpendicular to a central axis defining the base member.

17. The humeral prosthetic according to claim 14 wherein said fixation member defines a soft tissue fixation hole.

18. The humeral prosthetic according to claim 12 wherein the base defines a plurality of soft tissue fixation members.

19. A humeral prosthetic comprising:
a head portion having an articulating surface;
a base member coupled to said head portion defining an outer fixation surface, said base member having a locking mechanism;
a soft tissue fixation member having a coupling mechanism, wherein said coupling mechanism functions to couple the soft tissue fixation member to the base member, wherein said locking mechanism is configured to prevent movement of the soft tissue fixation member with respect to the base member; and
a tapered stem coupled to said base member, wherein said exterior surface defines a channel and wherein said locking mechanism is a flange configured to mate with said channel.

20. The humeral prosthetic according to claim 19 wherein said exterior surface defines a plurality of channels.

21. A humeral prosthetic comprising:
a head portion having an articulating surface;
a base member coupled to said head portion defining an outer fixation surface, said base member having a locking mechanism;
a soft tissue fixation member having a coupling mechanism, wherein said coupling mechanism functions to couple the soft tissue fixation member to the base, wherein said locking mechanism is configured to prevent movement of the soft tissue fixation member with respect to the base member;
a taper stem coupled to said base member, wherein said fixation member is a flange, wherein said fixation member defines a soft tissue fixation slot.

22. An orthopedic implant comprising:
a body which is at least partially implantable within a bone, said body having a cylindrical external surface and an articulating surface; and
an attachable means for coupling soft tissue to said cylindrical exterior surface, said attachable means for coupling soft tissues to the cylindrical external surface having an attachment mechanism, said attachment mechanism operable to prevent movement of the attachable means for soft tissue attachment with respect to the body, wherein said body is configured to be implanted into a bone to provide a complete implant.

23. The orthopedic implant according to claim 22 further comprising a bone fixation member coupled to said body.

24. The orthopedic device according to claim 22 wherein said attachment mechanism is selected from the group of a Morse type taper, a keyed slot, a keyed flange, a threaded fastener, and a polymer bone cement.

25. The orthopedic implant according to claim 22 wherein said means for coupling soft tissue is annularly disposed about said body.

26. The orthopedic implant according to claim 22 wherein the means for coupling the soft tissue is adjustably attached to the body.

27. The orthopedic implant according to claim 22 wherein said body is selected from the group of a prosthesis, a shoulder prosthesis, a knee prosthesis, a hip prosthesis, an elbow prosthesis, a tibia prosthesis, an intercalary member, and a bone strengthening member.

28. A method for implanting an orthopedic implant comprising:
selecting an appropriately sized implant having an articulating head and a body having a bone coupling mechanism;
determining if soft tissue fixation to the implant is necessary;
if soft tissue fixation is necessary, attaching a soft tissue fixation mechanism to the implant and implanting said implant; and
if soft tissue fixation is not necessary, implanting the implant without the soft tissue fixation mechanism.

29. The method for implanting an orthopedic device according to claim 28 wherein attaching said soft tissue fixation mechanism to said implant is disposing said soft tissue fixation member about said implant.

* * * * *